United States Patent [19]

Mazzocco

[11] 4,423,809
[45] Jan. 3, 1984

[54] PACKAGING SYSTEM FOR INTRAOCULAR LENS STRUCTURES

[75] Inventor: Thomas R. Mazzocco, Granada Hills, Calif.

[73] Assignee: Staar Surgical Company, Inc., Irwindale, Calif.

[21] Appl. No.: 400,664

[22] Filed: Jul. 22, 1982

Related U.S. Application Data

[63] Continuation-in-part of Ser. No. 346,105, Feb. 5, 1982.

[51] Int. Cl.³ .................. B65D 81/22; A61F 1/16; B65D 25/54; B65D 51/24
[52] U.S. Cl. .................. 206/5.1; 206/45.34; 206/210; 220/23; 3/13; 356/246
[58] Field of Search .............. 206/5.1, 210, 45.34, 206/205; 356/246; 220/23; 294/1 CA, 64; 3/13

[56] References Cited

U.S. PATENT DOCUMENTS

| | | | |
|---|---|---|---|
| 2,384,334 | 9/1945 | Olson | 294/64 |
| 2,615,448 | 10/1952 | Fields . | |
| 3,091,328 | 5/1963 | Leonardos | 206/5.1 |
| 3,150,406 | 9/1964 | Obitts | 206/5.1 |
| 3,168,100 | 2/1965 | Rich | 206/5.1 |
| 3,268,068 | 8/1966 | Le Grand | 206/5.1 |
| 3,304,113 | 2/1967 | Hutchison | 294/64 |
| 3,743,337 | 7/1973 | Crary | 294/1 CA |
| 3,822,780 | 7/1974 | Ulmer | 206/5.1 |
| 4,113,088 | 9/1978 | Binkhorst | 206/210 |
| 4,122,942 | 10/1978 | Wolfson | 206/5.1 |
| 4,136,406 | 1/1979 | Norris | 3/13 |
| 4,149,279 | 4/1979 | Poler | 206/5.1 |
| 4,173,281 | 11/1979 | Trought | 206/5.1 |
| 4,198,980 | 4/1980 | Clark | 3/13 |
| 4,205,747 | 6/1980 | Gilliam | 206/5.1 |
| 4,257,521 | 3/1981 | Poler | 206/5.1 |
| 4,269,307 | 5/1981 | LaHaye | 206/5.1 |
| 4,326,306 | 4/1982 | Poler | 206/5.1 |

Primary Examiner—William T. Dixson, Jr.
Attorney, Agent, or Firm—Frank Frisenda, Jr.

[57] ABSTRACT

The invention provides an improved autoclavable system for packaging of intraocular lens structures. In one embodied form, the inventive system comprises an outer container having at least two optically clear windows arranged in parallel relationship, an inner holding fixture mounted within the outer container for receiving and supporting an intraocular lens structure in alignment with the windows and a liquid medium within the container which substantially duplicates optical transmission characteristics of fluid in the eye. The unique packaging system provides an autoclavable sterile environment for a wide variety of intraocular lens structures prior to implantation which permits visual inspection and measurement of important optical parameters of the lens structure without removal of the lens from the container. Additionally, in a preferred embodiment of the invention, the lens holding fixture can also be used as a surgical tool and handling device for the intraocular lens during manufacture, inspection prior to implantation, and manipulation for placement of the intraocular lens structure within the eye.

23 Claims, 10 Drawing Figures

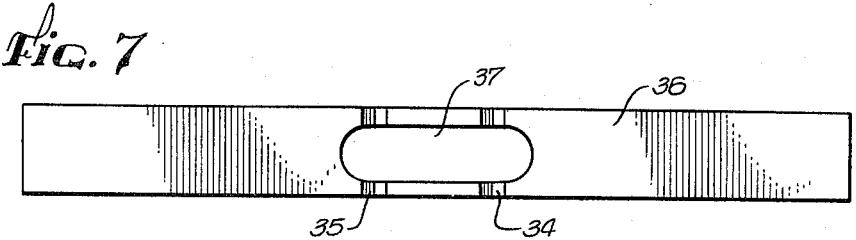
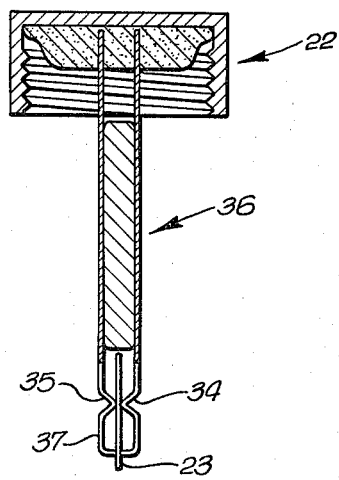
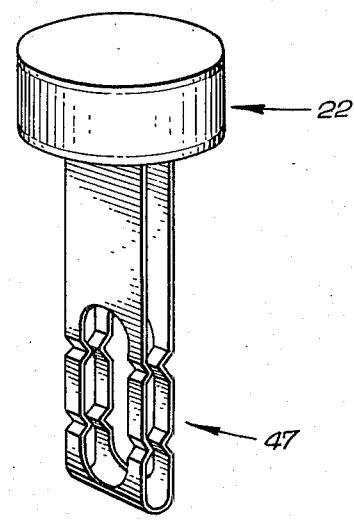
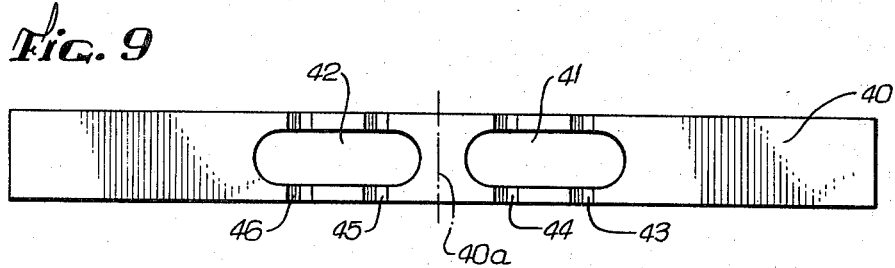
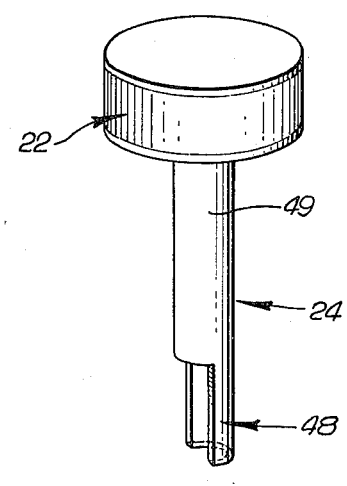

PACKAGING SYSTEM FOR INTRAOCULAR LENS STRUCTURES

CROSS-REFERENCE TO RELATED APPLICATIONS

This application is a continuation-in-part of my previously filed U.S. patent application Ser. No. 346,105, filed Feb. 5, 1982 for "Deformable Intraocular Lens Structures and Methods and Devices for Implantation", which disclosure is hereby incorporated by this reference.

BACKGROUND OF THE INVENTION

Intraocular lenses have gained wide acceptance in replacement of human crystalline lens after a variety of cataract removal procedures. The human crystalline lens is generally recognized to be a transparent structure having a thickness of about 5 millimeters and diameter of about 9 millimeters. The lens is suspended behind the iris by zonular fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may be generically categorized as intracapsular (in which the lens is removed together with the lens capsule) or extracapsular (in which the anterior capsule is removed with the lens, and the posterior capsule is left intact).

Since Ridley implanted the first artificial lens in 1949, the problems associated with cataract extraction and lens implantation have received a great deal of attention from ophthalmic surgeons.

Various types of artificial lenses have been proposed, and appropriate surgical procedures have been developed which strive to reduce patient discomfort and reduce post-operative complications. Reference is made in this connection to *Pseudophakos* by N. Jaffe, et al; "History of Intraocular Implants" by D. P. Choyce (Annals of Ophthalmology, October 1973); U.S. Pat. No. 3,991,426 issued to Flom on Nov. 16, 1976; and U.S. Pat. No. 4,092,743 issued to Kelman on Nov. 8, 1977 which disclosures are hereby incorporated by this reference.

One of the important optical parameters of any intraocular lens structure to be implanted is the diopter power necessary to correct refractive error of the human crystalline lens, for instance, after a cataract operation. In this context, it is also important that the intraocular lens structure be of appropriate type, size and configuration, possess proper optical finish and be free of workmanship defects, if the lens structure is to be successful in the correction of, or replacement of the human crystalline lens.

Sterile packaging systems for medical devices are disclosed for instance, in U.S. Pat. No. 4,113,088, issued to Binkhorst; in U.S. Pat. No. 4,269,307, issued to LaHaye; as well as in U.S. Pat. No. 4,257,521, issued to Poler. However, these systems have not generally allowed accurate visual inspection of the aforementioned important optical parameters of the intraocular lens structure prior to implantation while maintaining a sterile environment for the lens structure. In this respect, a number of conventional packaging systems actually obstruct visualization of the lens structure in this package.

Moreover, a number of conventional systems do not permit the lens structure to be sterilized, for instance, by gas, irridiation, or autoclaving while maintained in the package.

Additionally, conventional systems typically package the intraocular lens structure in a dry state. Accordingly, prior to implantation, it is necessary to remove the lens from the package and to convert the optical parameters of the lens in air to equivalent measurements when the lens is in place in the eye. This conversion has generally required the use of special instruments and/or conversion charts in order to determine the expected lens performance after implantation in the eye.

Thus, such conventional packaging systems for intraocular lenses have had a number of disadvantages from a practical standpoint including obstructing visual inspection of the lens in a sterile environment, and requiring subsequent conversion of important optical parameters after removal from the package. These drawbacks can lead to uncertain performance of the lens after implantation, undisclosed defective lenses which generally means increased discomfort to the patient, as well as increased expense for the surgery.

Accordingly, those skilled in the art have recognized a significant need for a packaging system for intraocular lens structures which allows the lens to be conveniently autoclaved, to be maintained in a sterile environment prior to implantation and which will allow the lens to be visually inspected for important optical parameters without removing the lens structure from the package. The present invention fulfills these needs.

SUMMARY OF THE INVENTION

This invention relates to an improved packaging system for intraocular lens structures of the type used, for instance, following cataract removal procedures. Briefly, and in general terms, the unique system comprises an outer container having at least two optically clear windows arranged in parallel relationship, an inner holding fixture mounted within the outer container for receiving and supporting an intraocular lens structure in alignment with the windows and a liquid medium within the container which substantially duplicates optical transmission characteristics of fluid in the eye.

Accordingly, the inventive packaging system provides an autoclavable sterile environment for a wide variety of intraocular lens structures prior to implantation, which permits visual inspection and measurement of important optical parameters of the lens structure without removal of the lens from the container.

In a presently preferred embodiment of the invention, the inner lens holding fixture of the unique packaging system can also serve as a surgical tool and handling device for the intraocular lens during manufacture, inspection prior to implantation and manipulation for placement of the lens by the surgeon within the eye.

In more detail, the presently preferred form of the lens holding fixture comprises a mounting member of relatively stiff, compliant material having means for receiving and removably engaging the intraocular lens structure and which can be also utilized as a cross-action forcep. When positioned within the outer container, the fixture provides substantially complete visual access to the lens (particularly with respect to the optical zone portion), by viewing the lens from the windows of the outer container. The mounting member may be suitably positioned within the outer container, for instance, in association with sealing means for the outer container.

The liquid medium of the inventive packaging system has the appropriate optical transmission characteristics, including refractive index such that the medium provides measurement of the optical parameters specifically, focal length (power) and/or resolution quality of the lens in an environment similar to the expected environment of the lens once implanted in the eye.

Accordingly, the unique system for intraocular lens structures in accordance with the present invention provides an autoclavable, sterile package prior to implantation, while at the same time, providing a packaging system designed to permit critical inspection and measurement of the lens structure without removal from the package. Moreover, in a preferred embodied form of the invention, the packaging system provides a lens holding fixture of multi-purpose function, including use as a surgical tool and handling device for the intraocular lens during manufacture, inspection and implantation of the lens in the eye.

BRIEF DESCRIPTION OF THE DRAWINGS

FIG. 6 is a cross-sectional view taken substantially along the line 6—6 of FIG. 5 and further illustrates the second embodied inner holding fixture mounted in association with means for sealing the outer container in accordance with the present invention;

FIG. 7 is a plan view of the inner holding fixture shown in FIG. 6 comprising a single piece mount of relatively stiff, compliant material which when folded about mid-section, provides an optical aperture and means for receiving an intraocular lens structure therein;

FIG. 8 is a perspective view of yet another embodied inner holding fixture in accordance with the present invention mounted in association with means for sealing the outer container;

FIG. 9 is a planned view of the lens holding fixture depicted in FIG. 8 which may generally be described as a single piece strap including two optical apertures and means for receiving an intraocular lens structure therein; and FIG. 10 is a perspective view of still another embodied inner holding fixture for the improved autoclavable packaging system for intraocular lens structures in accordance with the present invention.

DESCRIPTION OF THE PREFERRED EMBODIMENTS

The present invention provides an improved autoclavable packaging system for intraocular lens structures which generally comprises an outer container having at least two optically clear windows or apertures, an inner holding fixture mounted within the outer container for receiving and for supporting an intraocular lens structure in viewing alignment with the windows and a liquid medium within the container of appropriate optical transmission characteristics similar to that expected when the lens structure is implanted in the eye. The unique packaging system accordingly provides an autoclavable sterile environment for the intraocular lens structure prior to implantation, designed to permit visual inspection and measurement of important optical parameters of the lens structure without removal of the lens from the container.

Generally, intraocular lens structures include an optical zone portion, either of rigid construction or of the deformable type (in accordance with the invention disclosed in my original U.S. patent application Ser. No. 346,105, filed Feb. 5, 1982) and fixation appendages which may either be integral or non-integral with the optical zone portion of the lens. Those skilled in the art will readily appreciate that a wide variety appendages may be utilized, for instance, of the compressible integral support element type, angulated support appendages with respect to the plane of the optic, angulated compressible appendages with internal supporting elements, and the like.

Figure 1:
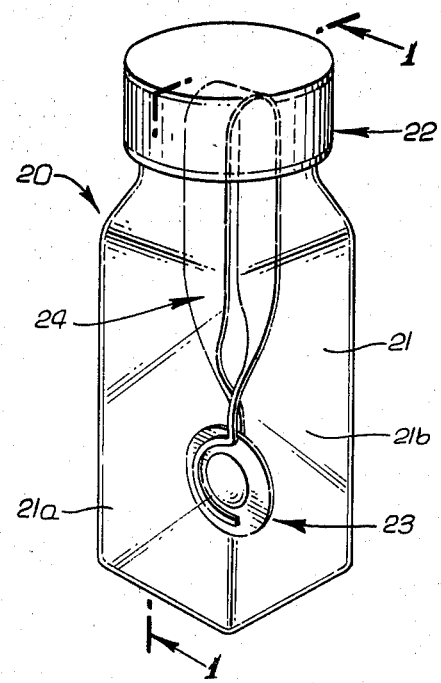
FIG. 1 is a perspective view of one embodied form of the improved autoclavable packaging system for intraocular lens structures in accordance with the present invention, the system including an outer container, and an inner holding fixture mounted within the outer container for receiving and for supporting an intraocular lens structure contained therein, and further including means for sealing the outer container.

Referring now to the drawing, denoted FIG. 1, there is shown one embodied form of the inventive packaging system (generally denoted 20) which may be described as an autoclavable outer container 21 comprising means for sealing the container 22, an intraocular lens structure 23 mounted within the lens holding fixture 24 and a specialized fluid medium (not shown). In more detail, the packaging system 20 comprises an outer container 21 having at least two optically clear windows or apertures 21a and 21b, arranged in parallel relationship with one another, an inner lens holding fixture 24 mounted within the outer container 21 for receiving and for supporting an intraocular lens structure 23 in viewing alignment with the windows 21a and 21b, and a liquid medium within the container (later described in more detail). The means 22 for sealing and for maintaining a sterile environment within the container 22, for instance, may be an appropriately configured stopper or cap 25 capable of integrating with the container 21 and effecting a hermetic seal.

The optically clear window(s) 21a and 21b may be of any suitable number to afford accurate visual inspection of the packaged lens structure. Suitable materials for fabricating the window(s) 21a and 21b, include both glass and plastics which will not distort measurements of the aforementioned important optical parameters of the intraocular lens including specifically the focal length (power) and/or resolution quality of the lens.

Figure 2:
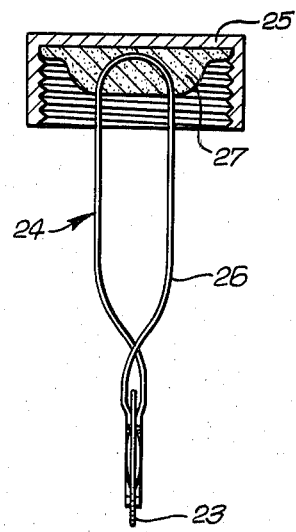
FIG. 2 is a cross-sectional view taken substantially along the line 1—1 of the inner holding fixture depicted in FIG. 1 which illustrates the mounting arrangement of the inner holding fixture and means for sealing the outer container in accordance with one embodied form of the present invention.
Figure 3:
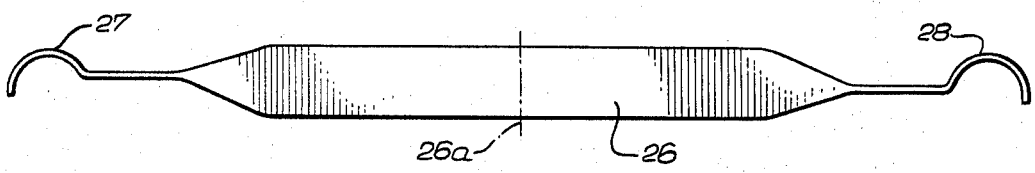
FIG. 3 is an enlarged plan view of a single piece mount of relatively stiff, compliant material, terminating at each end with an engagement bend, which when suitably configured yields an inner holding fixture which can also be utilized as a manipulation device similar to forceps of the cross-action type.
Figure 4:
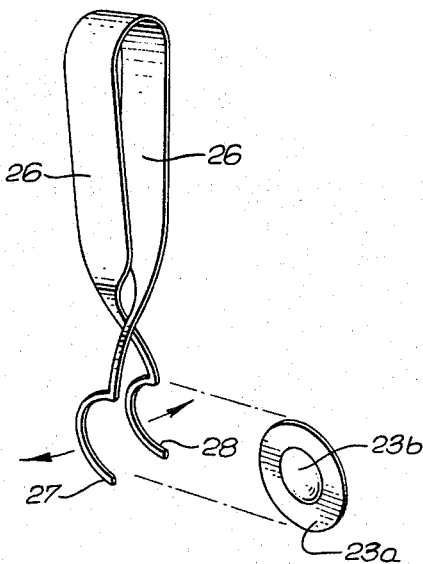
FIG. 4 is a perspective view of the inner holding fixture shown in FIGS. 2 and 3 in further detail and comprising means for receiving a portion of an intraocular lens structure while maintaining the optical zone portion of the lens in a visually unobstructed fashion.

As shown in FIG. 2, in one embodied form of the invention, the lens holding fixture 24 comprises a single piece mount 26 of relatively stiff, compliant material (as seen most clearly in FIG. 3), terminating at each end with an engagement bend 27 and 28. When appropriately configured, as shown in FIGS. 1, 2 and 4, the single piece mount 26 is folded at about its mid-section 26a and centrally disposed in the sealing means 22 of the outer container 21 with its engagement bends 27 and 28 disposed within the lower interior portion of the outer container 21.

Preferably, the lens holding fixture 24 is removable from the sealing means 22. Accordingly, the single piece mount 26, as shown in FIGS. 2-4, can also be utilized as a manipulation device wherein the engagement bends 27 and 28 act as forceps tips of the cross-action type. The embodied lens holding fixture 24 thus may also be used as a tool for the handling of the intraocular lens structure 23 during manufacturing, inspections, and/or by the surgeon during placement of the lens 23 within the eye.

In all forms, the embodied lens holding fixture 24 may be suitably disposed in the sealing means 22 of the outer container 21, for instance, by appropriately positioning the fixture 24 within the cap liner 27. Alternatively, the holding fixture 24 may be psoitioned within the outer container 21 in a fixed mount, separate from the sealing means 22. Of course, it is an important requirement that the lens holding fixture 24 be readily accessible and easily removed from the outer container 21 when necessary.

Figure 5:
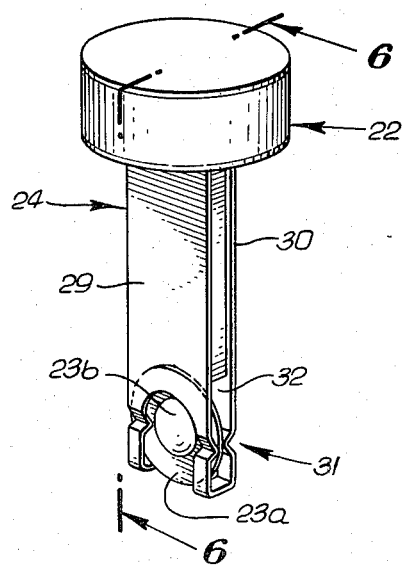
FIG. 5 is a perspective view of a second embodied inner holding fixture for receiving and for supporting an intraocular lens structure in accordance with the present invention.

As shown in FIG. 5, in a second embodied form of the invention, the lens holding fixture 24 comprises a pair of relatively rigid, compliant plates 29 and 30 suitably disposed in the means 22 for sealing of the outer container 21. The fixture 24 further comprises means (generally denoted 31) for receiving a portion of the intraocular lens structure 23, for instance, the periphery 23a of the lens 23 or support appendage (not shown), but maintains the optical zone portion 23b of the lens 23 in a visually unobstructed fashion aligned with the line of sight from the outer container window(s) 21a and 21b.

In more detail, the depicted means 31 for receiving and supporting the intraocular lens assembly 23 provided on the fixture 24 may generally be described as a recess 32 disposed at a distal end of the plates 29 and 30, having a pair of retaining indentations 34 and 35 at each side, which may exert a resilient compression force on at least a portion of the intraocular lens 23 to be held or which may retain at least a portion of intraocular lens 23 to be held via a free-floating manner. It is to be understood, however, that the configuration and size of the recess 32 may be widely varied and will be complimentary with the structure of the intraocular lens 23 to provide for removable engagement of the lens 23 from the fixture 24.

FIG. 6 illustrates the second embodied lens holding fixture 24. The cross-sectional view taken substantially along the line 6—6 of FIG. 5 illustrates the pair of relatively rigid, compliant plates 29 and 30 centrally disposed in the means 22 for sealing the outer container 21.

The lens holding fixture 24, as seen in FIG. 5, may be conveniently fabricated from a single piece strap 36 composed of a relatively rigid, compliant material (FIG. 7) having an oblong shaped, optical aperture 37 provided at about mid-section in the strap 36. Additionally, the strap 36 may be formed with appropriate retaining indentations 34 and 35 to provide for removable engagement of the intraocular lens structure to be retained once the strap 36 is appropriately folded at about its mid-section as seen in FIGS. 5 and 6.

FIGS. 8 and 9 show yet another embodied form of the lens holding fixture 24 which may be described as a single piece strap 40, including a pair of centrally disposed optical apertures 41 and 42 and means (generally denoted 47) for receiving and for retaining an intraocular lens 23 therein. The strap 40 as seen in FIG. 8 is folded upon itself at about mid-section 40a, with both optical apertures 41 and 42 suitably aligned for receiving and for supporting the intraocular lens thereof. The fixture 24 may be suspended from the top portion of the outer container 21, for instance, by provision made in association with the sealing means 22.

In still another embodiment shown in FIG. 10, the lens holding fixture 24 may comprise a hollow tube member 47 having means 48 for retaining an intraocular lens structure at the lower end of the tube member 49. The means 48 may be described as a half-section arcuate recess which suitably integrates with, for instance, a supporting appendage on the intraocular lens structure, typically of the compressible type. In the depicted embodiment shown in FIG. 10, the lens holding fixture 24 is suitably mounted in association with the outer container 21 sealing means 22.

As previously mentioned, it is an important requirement in all embodied forms of the invention that the lens holding fixture 24 provide an unobstructed view of the optical zone portion 23b of the lens 23. This allows the measurement of diopter power and inspection of size, optical finish and workmanship of the lens 23 without removal from the outer container 21.

Those skilled in the art will readily appreciate that the lens holding fixture, in accordance with the present invention, can be fabricated having a wide variety of specific shapes designed for removably engaging the intraocular lens structure, that is, by cooperating with an appendage, periphery or the optical zone portion of the lens itself.

The fluid medium within the outer container may be gaseous, liquid, or may be a combination thereof, which allows the intraocular lens structure to be autoclaved. It is an important feature of the medium in accordance with the present invention, that the medium provide appropriate optical transmission equivalent to that anticipated when the lens is implanted in the eye. This avoids the conversion of optical parameters from their measurement in air to their equivalent measurements in place in the eye. Suitable fluids in this regard include saline solution, distilled water, alcohol and the like.

Typically, the liquid medium will be a self-sterilizing fluid which is compatible with the components of the inventive packaging system, that is, media which will not interfere with for instance, polymer structure.

Accordingly, the improved autoclavable system for packaging of an intraocular lens structure having a peripheral lens portion and an optical zone portion for implantation within a human eye in accordance with the present invention comprises:

(a) an outer container having at least two optically clear windows arranged in substantially parallel relationship with each other;

(b) means for sealing and for maintaining a sterile environment within the outer container;

(c) means for receiving and for supporting the intraocular lens structure mounted within the outer container, the means integrating with the peripheral lens portion of the intraocular lens structure but maintaining the optical zone portion of the intraocular lens structure in a substantially complete visually unobstructed fashion aligned with the outer container windows thereby enabling the intraocular lens structure to be inspected from the outer container windows for prescribed optical parameters of the intraocular lens structure including type, size, configuration, optical finish and diopter power of the lens structure; and (d) A fluid medium within the container having appropriate optical transmission characteristics, wherein the inventive system for packaging the intraocular lens structure affords measurement of the optical parameters of the lens structure in an environment substantially similar to the expected environment of the lens structure once implanted in the eye while maintaining a sterile environment for the lens structure within the system for packaging.

The lens structure once implanted in the eye will have a refractive index of about aqueous. Intraocular lens structures in a dry state will typically have a refractive index in a range of from about 1.35 to about 1.55.

All components of the inventive packaging system are each made from autoclavable materials which are relatively inert with respect to one another. Suitable materials for use include glass, stainless steel or titanium, and polymeric materials such as silicone rubber, phenolic plastics, ABS plastics or the like.

Accordingly, the present invention fulfills the significant needs for a packaging system for intraocular lens structures which allows the lens to be conveniently autoclaved, to be maintained in a sterile environment prior to implantation, and which will allow the lens to be visually inspected for important optical parameters without removing the lens structure from the package.

Those skilled in the art will readily appreciate that other suitable shapes for the outer container and lens holding fixture may be utilized in accordance with the invention other than those specifically depicted. Of course, the materials, used for fabrication of the system components may be widely varied.

The described packaging system and lens structures are merely illustrative of specific embodiments in accordance with the invention.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. An improved autoclavable system for packaging of an intraocular lens structure having a peripheral lens portion and an optical zone lens portion for implantation within a human eye, said system comprising, in combination:

(a) an outer container having at least two optically clear windows arranged in substantially parallel relationship with one another;

(b) means for sealing and for maintaining a sterile environment within said outer container;

(c) means for receiving and for supporting said intraocular lens structure mounted within said outer container, said means integrating with said peripheral lens portion of said intraocular lens structure but maintaining said optical zone portion of said intraocular lens structure in a substantially complete visually unobstructed fashion aligned with said outer container windows thereby enabling the intraocular lens structure to be inspected from said outer container windows for prescribed optical parameters of said intraocular lens structure including type, size, configuration, optical finish and diopter power of said lens structure; and (d) a fluid medium within said outer container having appropriate optical transmission characteristics, wherein said system for packaging said intraocular lens structure affords measurement of said optical parameters of said lens structure in an environment substantially similar to the expected environment of said lens structure once implanted in the eye while maintaining a sterile environment for the lens structure within said system for packaging.

2. The improved packaging system as defined in claim 1 wherein said means for receiving and for supporting said intraocular lens is removable from said outer container.

3. The improved packaging system as defined in claim 1 wherein said means for receiving and for supporting said intraocular lens structure comprises a lens holding fixture mounted on a top portion of said outer container.

4. The improved packaging system as defined in claim 1 wherein said means for receiving and for supporting said intraocular lens structure is mounted in association with said sealing means.

5. The improved packaging system as defined in claim 1 wherein said lens holding fixture is separate from said sealing means.

6. The improved packaging system as defined in claim 1 wherein said means for receiving and for supporting said intraocular lens structure can be also utilized as a tool and handling device for the intraocular lens.

7. The improved packaging system as defined in claim 1 wherein said means for receiving and for supporting said intraocular lens structure comprises a pair of relatively rigid, compliant plates.

8. The improved packaging system as defined in claim 7 wherein said means for receiving and for supporting said intraocular lens structure further comprises at least one recess disposed at a distal end of said plates.

9. The improved packaging system as defined in claim 6 wherein said means for receiving and for supporting said intraocular lens structure can also be utilized as a cross-action forceps.

10. The improved packaging system as defined in claim 8 wherein said means for receiving and for supporting said intraocular lens structure further comprises a plurality of retaining indentations disposed on each of said plates which retain at least a portion of said intraocular lens structures to be held.

11. The improved packaging system as defined in claim 1 wherein said means for receiving and for supporting said intraocular lens structure comprises a relatively rigid, compliant, single piece mount folded at about mid-section.

12. The improved packaging system as defined in claim 11 wherein said means for receiving and for supporting said intraocular lens structure further comprises a pair of engagement bends provided on said single piece mount.

13. The improved packaging system as defined in claim 8 wherein said means for receiving and for supporting said intraocular lens structure comprises a recess disposed at a distal end of said plates, each of said plates having a pair of retaining indentations at each longitudinal side which retain at least a portion of said intraocular lens to be held.

14. The improved packaging system as defined in claim 1 wherein said means for receiving and for supporting said intraocular lens structure comprises at least one optical aperture.

15. The improved packaging system as defined in claim 1 wherein said fluid medium is gaseous.

16. The improved packaging system as defined in claim 1 wherein said fluid medium is liquid.

17. The im packaging system as defined in claim 1 wherein said fluid medium is a combination of gas and liquid.

18. The improved packaging system as defined in claim 1 wherein said environment substantially similar to the expected environment includes a refractive index in the range of from about 1.30 to about 1.40.

19. The improved packaging system as defined in claim 18 wherein said fluid medium comprises saline solution.

20. The improved packaging system as defined in claim 18 wherein said fluid medium comprises distilled water.

21. The improved packaging system as defined in claim 18 wherein said fluid medium comprises alcohol.

22. The improved packaging system as defined in claim 1 wherein said means for receiving and for supporting said intraocular lens structure comprises a hollow tube member having means for retaining at least a portion of an intraocular lens structure at a lower end of said tube member.

23. The improved packaging system as defined in claim 22 wherein said means for retaining said intraocular lens structure is a half-section arcuate recess which integrates with a supporting appendage of said intraocular lens structure to be held.

* * * * *